US006359012B1

(12) United States Patent
Meckler et al.

(10) Patent No.: US 6,359,012 B1
(45) Date of Patent: Mar. 19, 2002

(54) METHOD FOR MAKING 24(S)-HYDROXYVITAMIN $D_2$

(75) Inventors: Harold Meckler, Delmar; Mark A. Helle, Westerlo; William B. Geiss, Athens; Brian T. Gregg, Voorheesville, all of NY (US)

(73) Assignee: Bone Care International, Inc., Middleton, WI (US)

( * ) Notice: Subject to any disclaimer, the term of this patent is extended or adjusted under 35 U.S.C. 154(b) by 0 days.

(21) Appl. No.: 09/470,581

(22) Filed: Dec. 22, 1999

(51) Int. Cl.[7] .................. C07C 40/00; C07C 403/00; A61K 31/592; A61K 31/593

(52) U.S. Cl. .................. 514/653; 552/653; 514/167

(58) Field of Search .................. 552/653; 514/167

(56) References Cited

U.S. PATENT DOCUMENTS

| | | | |
|---|---|---|---|
| 4,260,549 A | 4/1981 | DeLuca et al. | 260/397.2 |
| 4,391,802 A | 7/1983 | Suda et al. | 424/236 |
| 4,554,106 A | 11/1985 | DeLuca et al. | 260/397.2 |
| 4,749,710 A | 6/1988 | Truitt et al. | 514/167 |
| 4,758,383 A * | 7/1988 | Tachibana | 260/397.2 |
| 5,518,725 A | 5/1996 | Daynes et al. | 424/212.1 |
| 5,540,919 A | 7/1996 | Daynes et al. | 424/85.2 |
| 5,559,107 A | 9/1996 | Gates et al. | 514/167 |
| 5,562,910 A | 10/1996 | Daynes et al. | 424/278.1 |
| 5,589,471 A | 12/1996 | Hansen et al. | 514/167 |

FOREIGN PATENT DOCUMENTS

WO 9824800 * 6/1998

OTHER PUBLICATIONS

Manchand, Percy S., G. P. Yiannikouros, P. S. Belica and P. Madan, "Nickel–Mediated Conjugate Addition. Elaboration of Calcitriol from Ergocalciferol", *J. Org. Chem.*, 60, 6674–6581 (1994).

Miller, G. J., G. E. Stapleton, J. A. Ferrara, M. S. Lucia, S. Pfister, T. E. Hedlund and P. Upadhya, "The Human Prostatic Carcinoma Cell Line LNCaP Expresses Biologically Active, Specific Receptors for 1α,25–Dihydroxyvitamin $D_3$", *Cancer Research*, 52, 515–520 (Feb. 1, 1992).

Holick, M. F., H. K. Schnoes and H. F. DeLuca, "Identification of 1,25–Dihydroxycholecalciferol, a Form of Vitamin $D_3$ Metabolically Active in the Intestine", *Proc. Nat. Acad. Sci. USA*, vol. 68, No. 4, pp. 803–804 (Apr. 1971).

Holick, M. F., E. J. Semmler, H. K. Schnoes and H. F. DeLuca, "1αHydroxy Derivative of Vitamin $D_3$: A Highly Potent Analog of 1α,25–Dihydroxyvitamin $D_3$", *Science*, vol. 180, pp. 190–191 (Apr. 1973).

Jones, Glenville, H. K. Schnoes and H. F. DeLuca, "Isoloation and Identification of 1,25–Dihydroxyvitamin $D_2$", *Biochemistry*, vol. 14, No. 6, pp. 1250–1256 (1975).

Jones, Glenville, H. K. Schnoes, L. Levan and H. F. DeLuca, "Isolation and Identification of 24–Hydroxyvitamin $D_2$ and 24,25–Dihydroxyvitamin $D_2$", *Archives of Biochemistry and Biophysics*, vol. 202, No. 2, pp. 450–457 (1980).

Lam, H. Y. Peter, H. K. Schnoes and H. F. DeLuca, "1α–Hydroxyvitamin $D_2$: A Potent Synthetic Analog of Vitamin $D_2$", *Science*, vol. 486, No. 4168, pp. 1038–1040 (Dec. 1974).

Skowronski, Roman J., D. M. Peehl and D. Feldman, "Actions of Vitamin $D_3$ Analogs on Human Prostate Cancer Cell Lines: Comparison with 1,25–Dihydroxyvitamin $D_3$", *Endocrinology*, vol. 136, No. 1, pp. 20–26 (1995).

(List continued on next page.)

*Primary Examiner*—Sabiha Qazi
(74) *Attorney, Agent, or Firm*—Michael Best & Friedrich LLP; Teresa J. Welch

(57) ABSTRACT

The invention provides a method for making 24(S)-hydroxyvitamin $D_2$ which is a stereospecific synthesis.

4 Claims, 8 Drawing Sheets

OTHER PUBLICATIONS

Mawer, E. Barbara, G. Jones, M. Davies, P. E. Still, V. Byford, N. J. Schroeder, H. L. J. Makin, C. W. Bishop and J. C. Knutson, "Unique 24–Hydroxylated Metabolites Represent a Significant Pathway of Metabolism of Vitamin $D_2$ in Humans: 24–Hydroxyvitamin $D_2$ and 1,24–Dihydroxyvitamin $D_2$ Detectable in Human Serum", *JCE&M*, vol. 83, No. 6, pp. 2156–2166 (Jun. 1998).

Seebach, Dieter, R. Naef and G. Calderari, "α–Alkylation of α–Heterosubstituted Carboxylic Acids Without Racemization", *Tetrahedron*, vol. 40, No. 8, pp. 1313–1324 (1984).

Baggiolini et al. (J. Am. Chem. Society. (1982), 104, 2945–2948).*

* cited by examiner

METHOD FOR MAKING 24(S)-HYDROXYVITAMIN $D_2$

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

This invention relates to a stereospecific synthesis of 24(S)-hydroxyvitamin $D_2$ which is, in effect, a prodrug for 1α,24(S)-dihydroxyvitamin $D_2$, a natural metabolite of vitamin $D_2$ that has been shown to have highly significant biologic effects, with a large therapeutic index when administered to a subject.

Vitamin D has long been established as having an important biological role in bone and mineral metabolism. For example, vitamin D plays a critical role in stimulating calcium absorption and regulating calcium metabolism. More recently, other roles for vitamin D have come to light. Specific nuclear receptors for 1α,25-dihydroxyvitamin $D_3$, the natural hormone form of vitamin $D_3$, have been found in cells of diverse organs not involved in calcium homeostasis. For example, Miller et al., 52 *Cancer Res.* (1992) 515–520, have demonstrated biologically active, specific receptors for 1α,25-dihydroxyvitamin $D_3$ in the human prostatic carcinoma cell line, LNCaP.

Still other metabolic conditions in which it has been suggested that vitamin D plays a role are immune response (see, e.g., U.S. Pat. No. 4,749,710 issued to Truitt et al.; U.S. Pat. No. 5,559,107 issued to Gates et al.; U.S. Pat. Nos. 5,540,919, 5,518,725 and 5,562,910 issued to Daynes et al.) and inflammatory response (see, e.g., U.S. Pat. No. 5,589,471 issued to Hansen et al.).

The discovery of active forms of vitamin D (M. F. Holick et al., 68 *Proc. Natl. Acad. Sci. USA*, 803–804 (1971); G. Jones et al., 14 *Biochemistry*, 1250–1256 (1975)), and active vitamin D analogs (M. F. Holick et al., 180 *Science* 190–191 (1973); H. Y. Lam et al., 186 *Science* 1038–1040 (1974)) in the 1970's caused much excitement and speculation about the usefulness of these vitamin D compounds in the treatment of bone depletive disorders, and later in treatment of other disease states such as inhibition of malignant cell proliferation (see, e.g., U.S. Pat. No. 4,391,802 issued to Suda et al.; Skowronski et al., 136 *Endocrinology* (1995) 20–26).

However, it has been found that active vitamin D compounds, particularly 1α-hydroxylated vitamin $D_3$ compounds, can produce dangerously elevated blood calcium levels due to their inherent calcemic activity. Because of this toxicity, 1-hydroxylated vitamin $D_3$ compounds can only be administered at dosages that are, at best, modestly beneficial, for example, in preventing or treating loss of bone or bone mineral content.

Considering the diverse biological actions of vitamin D and its potential as a therapeutic agent, a need exists for vitamin D compounds with greater specificity of activity and selectivity of action, e.g., vitamin D compounds with antiproliferative and differentiating effects but which have less calcemic activity than therapeutic amounts of the known compounds or analogs of vitamin $D_3$.

Interest has grown in the use of so-called prodrugs or compounds which when administered are metabolized to known active vitamin D compounds. With this interest, the need for straightforward, efficient syntheses of vitamin D prodrugs, especially 24-hydroxylated vitamin D compounds, has intensified. Very few methods for 24-hydroxylation of vitamin D compounds have been reported. See, e.g., Jones et al., 202 *Arch. Biochem. Biophys.* (1980) 450–457 and Mawer et al., 83 *J. Clin. Endo. Metab.* (1998) 2156–2166 which disclose a biologically generated 24-hydroxyvitamin $D_2$. Such biological syntheses compared to chemical syntheses are inefficient and require extremely large numbers of animal hosts to produce small amounts of desired compound. The art thus has yet to respond with a straightforward method for the synthesis of 24-hydroxyvitamin D compounds, particularly, 24-hydroxyvitamin $D_2$.

BRIEF SUMMARY OF THE INVENTION

The present invention provides a heretofore unmet need by the prior art, and specifically to the inherent inadequacies of prior synthetic processes for preparing 24-hydroxylated vitamin D compounds, specifically 24-hydroxyvitamin $D_2$ wherein the hydroxyl group at the carbon-24 position is in the (S) configuration. The method of the present invention is distinguished by its simplicity in that it eliminates certain separatory steps of diastereomers characteristic of prior art processes.

The product compound of the method of the present invention is represented by formula (1), shown hereinafter, and is 24(S)-hydroxyvitamin $D_2$ which has potent biological activity but low calcemic activity relative to the active forms of vitamin $D_3$. Preferably, such compound is a 24-hydroxylated prodrug which is hydroxylated in vivo at the C-1 position to form 1,24(S)-dihydroxylated active vitamin $D_2$.

The method of the present invention includes coupling of (S)-(+)-2,3-dimethyl-2-triethylsilyloxybutyraldehyde and a vitamin D phosphine oxide derivative to form a C-3 and C-24 diprotected trans-vitamin $D_2$ which is then deprotected and irradiated to yield the 24(S)-hydroxyvitamin $D_2$.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWING(S)

The preferred exemplary embodiment of the present invention will hereinafter be described in conjunction with the appended drawings wherein like designations refer to like elements throughout and in which.

DETAILED DESCRIPTION OF THE INVENTION

The present invention relates to 24(S)-hydroxyvitamin D$_2$ and a stereospecific synthesis thereof. Accordingly, the present invention will now be described in detail with respect to such endeavors; however, those skilled in the art will appreciate that such a description of the invention is meant to be exemplary only and should not be viewed as limitative on the full scope thereof.

The present invention provides 24(S)-hydroxyvitamin D$_2$, which finds value as a pharmaceutical agent. The compound is suitably a prodrug for 1α,24(S)-dihydroxylated vitamin D$_2$ 24(S)-hydroxyvitamin D$_2$ is hydroxylated in vivo at the 1α-position to become an active form of vitamin D$_2$. As a prodrug, the compound, in effect, bypasses the first-pass concern over intestinal vitamin D receptor binding which mediates intestinal calcium absorption, thereby resulting in reduced or no hypercalcemia compared with similar dosing with known active vitamin D compounds such as 1α,25-dihydroxyvitamin D$_3$.

In the following description of the method of the invention, process steps are carried out at room temperature and atmospheric pressure unless otherwise specified.

As used herein, the terms "substantially pure" or "substantially free" refer to a purity of at least 90%.

The method of the present invention provides 24(S)-hydroxyvitamin D$_2$ represented by formula (1):

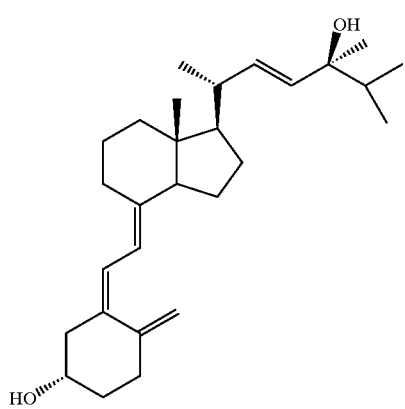

Figure 1:
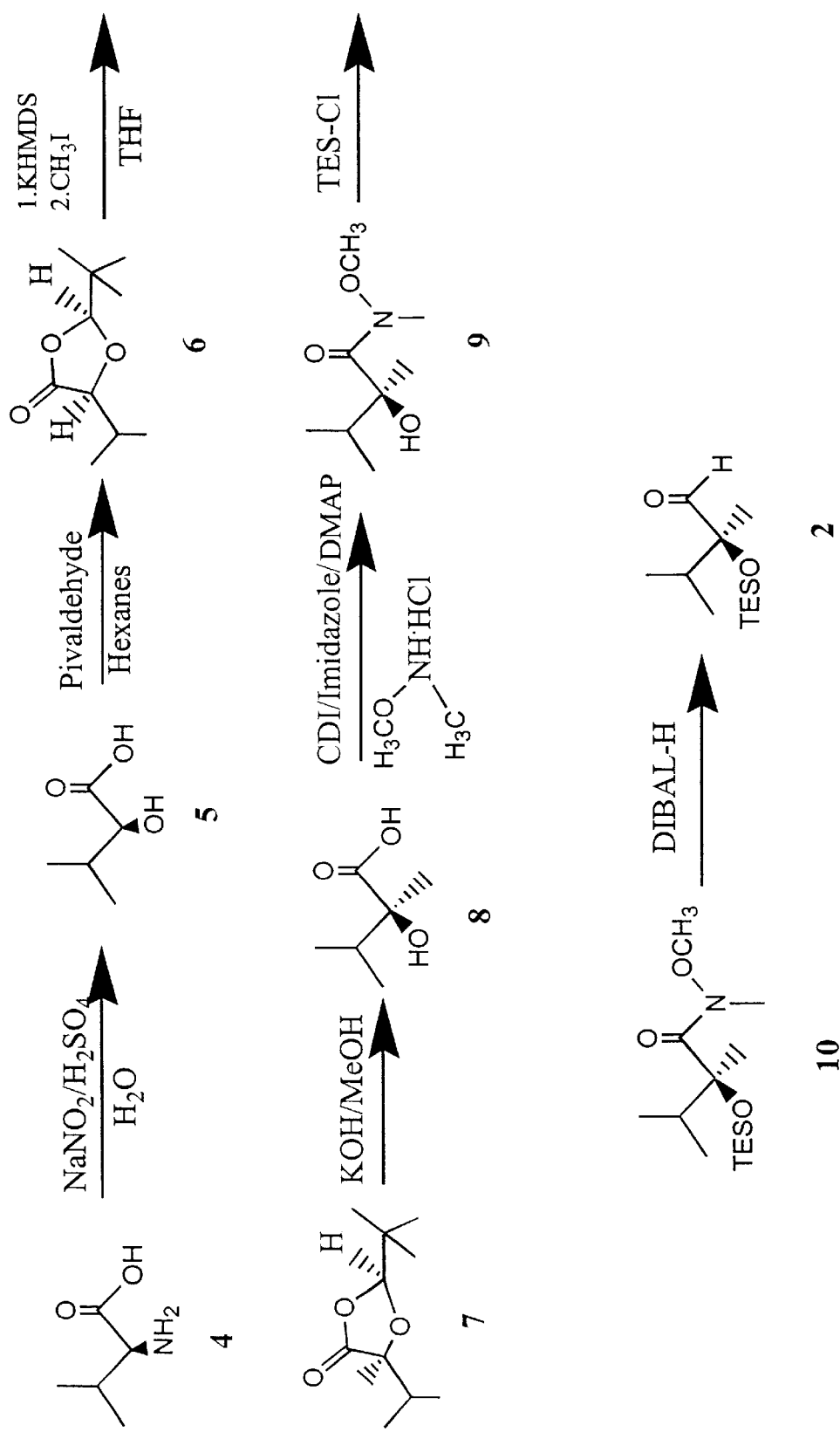
FIG. 1 illustrates the reaction scheme for preparing (S)-(+)-2,3-dimethyl-2-triethylsilyloxybutyraldehyde.
Figure 2:
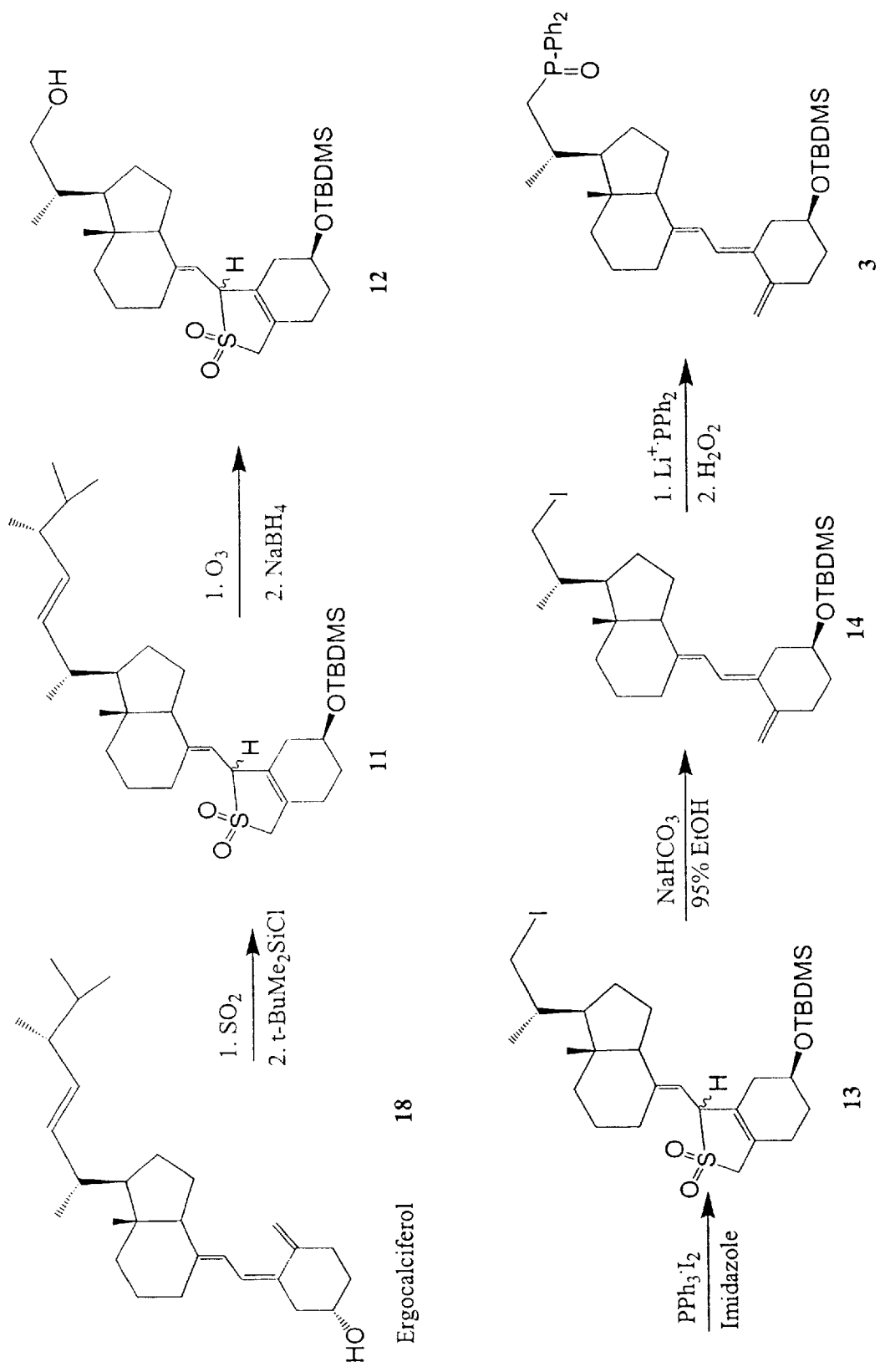
FIG. 2 illustrates a reaction scheme for preparing a vitamin D phosphine oxide from vitamin $D_2$.
Figure 3:
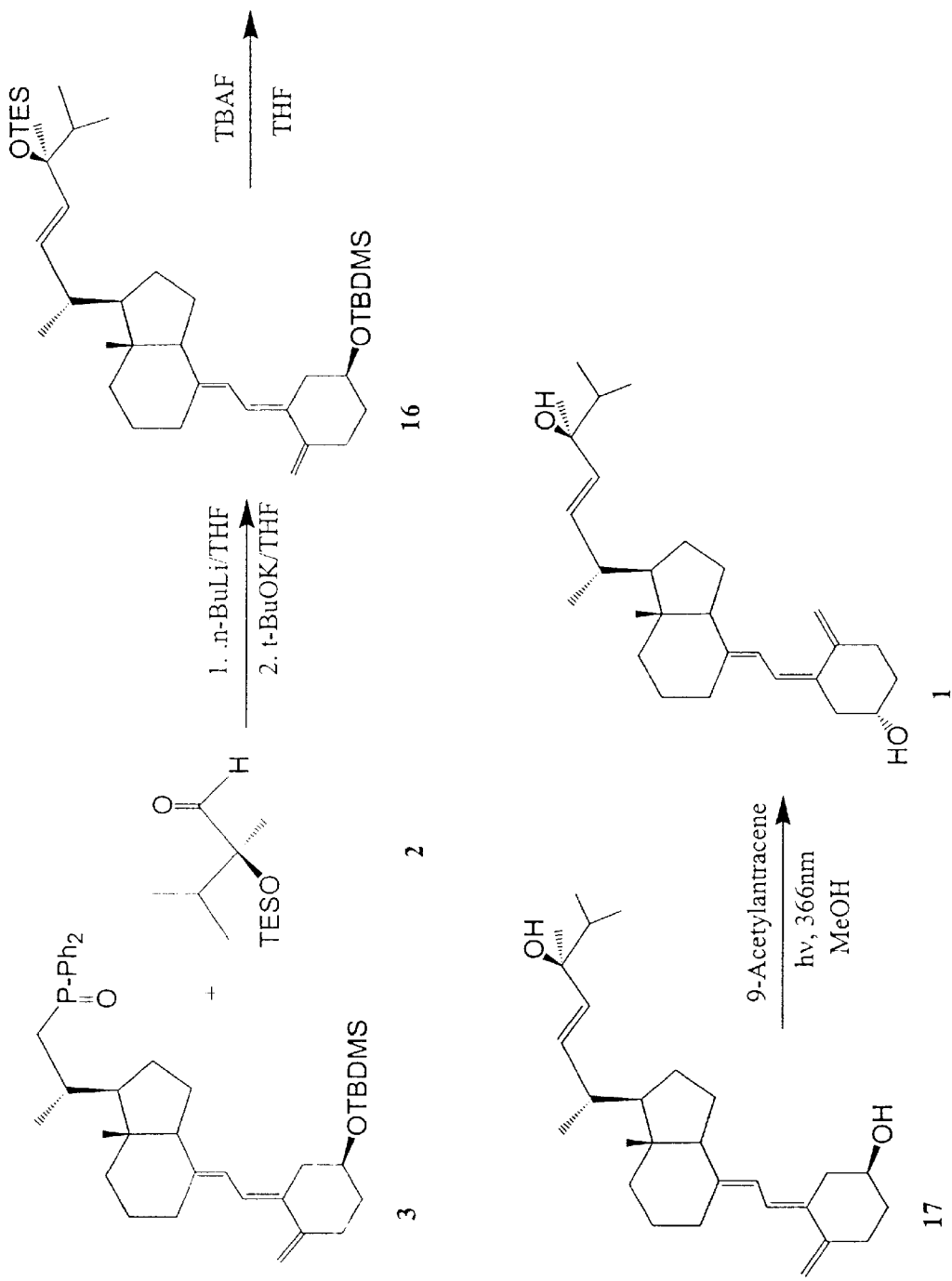
FIG. 3 illustrates the preparation of 24-hydroxyvitamin $D_2$ by coupling (S)-(+)-2,3-dimethyl-2-triethylsilyloxybutyraldehyde and a vitamin D phosphine oxide derivative.

The compound of formula (1) may generally be prepared by the stereospecific reaction process depicted in FIGS. 1–3. The synthesis is achieved through a Wittig-Horner coupling between two key intermediates, (S)-(+)-2,3-dimethyl-2-triethylsilyloxybutyraldehyde (2)

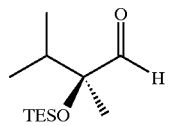

and a vitamin D phosphine oxide derivative (3)

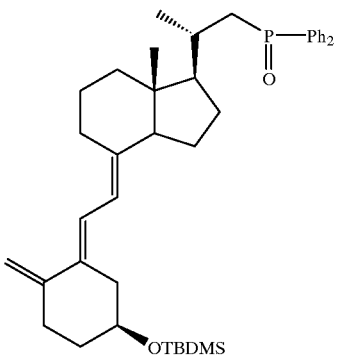

FIG. 1 illustrates a method of preparing (S)-(+)-2,3-dimethyl-2-triethylsilyloxybutyraldehyde (2) from L-(+)-valine (4) using a modification of a Seebach method or protocol (Seebach, D., et al., 40 Tetrahedron (1984)1313). The Seebach approach utilizes (S)-(+)-hydroxyisovaleric acid (5) as the starting substrate. (S)-(+)-Hydroxyisovaleric acid is commercially available but its cost raises a significant barrier to scale up synthesis which must be ultimately considered in the marketability of a pharmaceutical. Thus, the use of readily available, low cost amino acid L-(+)-valine (4) as the starting substrate provides significant cost efficiencies.

FIG. 2 illustrates a method for preparing the vitamin D phosphine oxide (3) using vitamin D$_2$ (or ergocalciferol) (18) as a starting material. FIG. 3 illustrates the method of the present invention for coupling of (S)-(+)-2,3-dimethyl-2-triethylsilyloxybutyraldehyde (2) and a vitamin D phosphine oxide derivative (3) and forming 24(S)-hydroxyvitamin D$_2$ (1). It is understood that the method of the present invention has significant advantages over prior art syntheses which yield diastereomers of the 24(S) and 24(R)-hydroxy compounds and then depend upon separation of diastereomers to yield the 24(S)-hydroxyvitamin D$_2$ diastereomer. Such separation, while seemingly simple in concept, has been very difficult in real world technique, and yields are not of the magnitude that readily affords a synthetic method to be scaled up for production purposes. The method of the present invention directly provides, in contrast, stereochemical purity in the form of the stereospecific end product 24(S)-hydroxyvitamin D$_2$. Hereinafter when reference is made to the 24-hydroxy compound, unless otherwise specified, it will be presumed that the compound is the (S) configuration.

Reference is now made to FIG. 1 where L-(+)-valine (4) is converted to (S)-(+)-2,3-dimethyl-2-triethylsilyloxybutyraldehyde (2) via a seven-step process. Specifically, L-15 (+)-valine (4) is first converted to (S)-(+)-hydroxyisovaleric acid (5). The conversion is suitably accomplished by reaction with nitrous acid and hydrolysis with retention of configuration of the unstable diazonium salt intermediate; more preferably the nitrous acid is produced in situ from sodium nitrite and sulfuric acid, which generates an unstable diazonium salt; the diazonium salt undergoes hydrolysis under the reaction conditions. (S)-(+)-hydroxyisovaleric acid (5) is subjected to an acid-catalyzed condensation with pivaldehyde in hexanes to yield a dioxolane (6) as a mixture of cis/trans isomers in a 20:1 ratio. The dioxolane (6) is then deprotonated in the 5-position and selectively alkylated with methyl iodide to yield a 5-methyldioxolane (7). The deprotonation is suitably accomplished utilizing potassium hexamethyldisilazide (KHMDS), although other strongly basic deprotonating agents are possible, e.g., lithium diisopropylamide (LDA) or lithium hexamethyldisilazide (LHMDS).

The 5-methyldioxolane (7) is then hydrolyzed to yield (S)-(+)-2,3-dimethyl-2-hydroxybutyric acid (8). This hydrolysis is suitably accomplished utilizing potassium hydroxide (KOH) in water/methanol (MeOH). (S)-(+)-2,3-dimethyl-2-hydroxybutyric acid (8) is then converted to a methylated 2-hydroxybutyramide (9), 2(S)-(+)-N-methyoxy-N-methyl-2,3-dimethyl-2-hydroxybutyramide, a so-called "Weinreb amide". The conversion proceeds with the addition of 1,1-carbonyldiimidazole (CDI) followed by imidazole, N,O-dimethylhydroxylamine hydrochloride and 4-dimethylaminopyridine (DMAP). The amide (9) is then silylated suitably using triethylsilyl chloride (TES-Cl) to yield a triethylsilyl-protected butyramide (10). This protected amide (10) is then reduced to yield the (S)-(+)-2,3-dimethyl-2-triethylsilyloxybutyraldehyde (2). The reduction is suitably accomplished utilizing diisobutylaluminum hydride (DIBAL-H). Although other hydride reducing agents are possible, e.g., red-Al(Vitride) or lithium tri-tertbutoxyaluminum hydride (LiAl(OtBu)$_3$H).

Reference is now made to FIG. 2 wherein vitamin $D_2$ is converted to a vitamin D phosphine oxide (3). Vitamin $D_2$ is first converted to an iodide (14) and then to the phosphine oxide (3). Specifically, vitamin $D_2$ (18) is treated with $SO_2$ to afford a mixture of C-6/C-9 epimeric $SO_2$ adducts which are then silylated to afford a C-3 protected adducts (11). The C-3 protected adducts (11) then undergo ozonolysis and direct reduction to a C-22 alcohol (12). The reduction is suitably accomplished with sodium borohydride (NaBH$_4$). The C-22 alcohol (12) is then iodinated (I$_2$/PPh$_3$/imidazole) and subjected to $SO_2$ extrusion, suitably using sodium bicarbonate in 95% ethanol, to yield a C-3 protected vitamin D iodide (14). The C-3 protected vitamin D iodide (14) is then converted to the phosphine oxide (3) by sequential treatment with lithium diphenylphosphide (LiPPh$_2$), followed by oxidation with hydrogen peroxide.

Reference is now made to FIG. 3 wherein the (S)-(+)-2,3-dimethyl-2-triethylsilyloxybutyraldehyde (2) and a vitamin D phosphine oxide derivative (3) are coupled to subsequently yield 24(S)-hydroxyvitamin $D_2$ (1). The coupling of (S)-(+)-2,3-dimethyl-2-triethylsilyloxybutyraldehyde (2) and a vitamin D phosphine oxide derivative (3) followed by elimination initially yields a trans-C-22-olefin (16). The coupling is undertaken with n-butyl lithium (n-BuLi) in tetrahydrofuran (THF) followed by potassium tert-butoxide (t-BuOK). The trans-C-22-olefin (16) is then deprotected to yield trans-24(S)-hydroxyvitamin $D_2$ (17) by the removal of the silyl protecting group. This step is suitably accomplished utilizing tetrabutylammonium fluoride (TBAF) in THF. The final step entails the photochemical isomerization of the trans-24(S)-hydroxyvitamin $D_2$ (17) to the cis-24(S)-hydroxyvitamin $D_2$ (1). This isomerization is carried out with 9-acetylanthracene as a sensitizer and irradiated with 366 nm light. Subsequent recrystallization yields a white crystalline product.

The compound of the present invention has potential as the active compound in pharmaceutical compositions having reduced side effects and low toxicity as compared with the known analogs of active forms of vitamin $D_3$. The compound of the present invention is of particular value as a prodrug in which it undergoes hydroxylation at the 1α-position of the A-ring of the vitamin D ring structure, thus providing an active form of vitamin $D_2$ compound which is 1α,24-dihydroxylated. As to 24(S)-hydroxyvitamin $D_2$, little or no first-pass interaction with the intestinal vitamin D receptors is to be expected, thus yielding little or no stimulation of intestinal calcium absorption.

The present invention is further explained by the following examples which should not be construed by way of limiting the scope of the present invention. All nonaqueous reactions were performed under an atmosphere of dry nitrogen. Reagents purchased from commercial sources were used as received, unless noted otherwise. Anhydrous tetrahydrofuran was obtained by the distillation of tetrahydrofuran in the presence of sodium metal and benzophenone ketyl. Proton magnetic resonance spectra were obtained on a Bruker AC 300 MHz NMR, using tetramethylsilane as an internal reference. Infrared spectra were recorded with a Perkin-Elmer Spectrum 1000 spectrophotometer. Mass spectra analyses were performed on a Shimadzu QP-5000 GC/MS (CI mass spectrometry). Optical rotations were measured with a Perkin-Elmer 243B Polarimeter in a 1-cm cell. Optical purities were analyzed on a Spectra-Physics HPLC system with a Chiralpak AD column (4.6×250 mm, Daicel Chemical Industries, Ltd.), with a mobile phase of 60:40 hexanes:ethanol containing 0.2% ethylamine at a flow rate of 1.0 mL/minute, and UV detection at 254 nm. Thin layer chromatography (TLC) was performed using 1"×3" Whatman 60A (0.025 mm thick) silica gel plates. Visualization of TLC plates was realized by observation under a UV lamp, by dipping in saturated ceric ammonium sulfate solution in 50% aqueous sulfuric acid or commercial phosphomolybdic acid in acidic ethanol. Melting points were obtained on an Electrothermal capillary melting point apparatus.

EXAMPLE 1

Synthesis of (S)-(+)-2,3-Dimethyl-2-triethylsilyloxybutyraldehyde (2)

Preparation of (S)-(+)-Hydroxyisovaleric Acid (5)

A 12-L, three-neck, round-bottom flask equipped with an addition funnel and a thermometer was charged with L-(+)-valine (4) (710 g, 6.1 moles). Water (3 L) was added forming a suspension. Concentrated sulfuric acid (314 g, 6.14 moles) was added slowly with stirring, affording a clear solution. Ice (2 kg) was added to the solution, cooling the solution to below 5° C. Cooling was aided by the use of an external ice bath. Sodium nitrite (44 g, 6.2 moles) was added slowly, as a solution in water (2 L). The solution was kept below 5° C. with the addition of ice. When the addition of sodium nitrite was complete, the solution was allowed to warm to room temperature slowly overnight. The pH of the solution was adjusted to 3–4 by the slow addition of solid sodium bicarbonate, and then extracted with ethyl acetate (3×2 L). The combined organic solution was dried with magnesium sulfate, filtered through Celite™, and concentrated. The residue was recrystallized from ethyl acetate/hexanes (3:1) to yield 212 g (30%) of (S)-(+)-hydroxyisovaleric acid (5) as a white crystalline solid. The mother liquor was concentrated and the residue recrystallized from ethyl acetate/hexanes to yield an additional 186 g (26%). The total yield of desired product was 56%. The $^1$H NMR spectrum of the product (5) was consistent with that of the commercial material.

Preparation of (2S,5S)-2-(tert-butyl)-5-isopropyl-1,3-dioxolan-4-one (6)

To a suspension of (5) (97 g, 0.82 mol) in hexanes (800 mL) in a 2-L, one-neck, round-bottom flask was added trimethylacetaldehyde (100 g, 1.16 mol, 1.4 equivalents) and p-toluene sulfonic acid (1 g). The flask was equipped with a magnetic stir bar, a Dean-Stark trap, and a reflux condenser. The reaction mixture was heated under reflux until approximately 15 mL of water was collected. Heating was discontinued and the colorless solution was allowed to cool to room temperature. The reaction solution was poured into saturated aqueous sodium bicarbonate solution (400 mL). The layers were separated and the aqueous layer extracted with ethyl acetate (400 mL). The combined organics were dried over anhydrous magnesium sulfate, filtered, and the solvent removed in vacuo to afford a colorless oil (151 g). Crystallization from hexanes provided 126 g (82% yield) of (6) as white crystals. The $^1$H NMR of the product was consistent with the structure.

Preparation of (2S,5R)-2-(tert-butyl)-5-methyl-5-isopropyl-1,3-dioxolan-4-one (7)

A 12-L, three-neck, round-bottom flask equipped with a mechanical stirrer, nitrogen bubbler, pressure equalizing addition funnel, and a thermocouple was charged with dry THF (3.5 L). To this was added potassium hexamethyldisilazide (0.5M solution in toluene, 1.6 L, 1.2 equivalents). The resulting solution was cooled to −78° C. and a solution of (6) (126 g, 0.67 mol in dry THF (400 mL)) was added. The resulting yellow solution was allowed to stir for 45 minutes at which point methyl iodide (139 g, 0.96 mol, 1.4 equivalents) was added. The reaction mixture was allowed to slowly warm to −30° C. over 3.5 hours. After this time, the reaction was quenched with saturated aqueous ammonium chloride solution (2 L) and extracted with ether (2×2 L). The combined organics were dried over anhydrous magnesium sulfate and filtered through a Celite™ pad. The filtrate was evaporated in vacuo to afford a crude orange oil. This was dissolved in ethyl acetate (200 mL) and filtered through a plug of silica gel. The solvent was removed in vacuo providing a clear orange oil (141 g). Crystallization from hexanes afforded 104 g (78% yield) of (7) as pale yellow crystals. The $^1$H NMR spectrum of the product was consistent with the structure.

Preparation of (S)-(+)-2,3-dimethyl-2-hydroxybutyric acid (8)

To a magnetically stirred solution of (7) (94 g, 0.47 mol) in methanol (450 mL) and water (100 mL), in a 1-L, one-neck, round-bottom flask was added potassium hydroxide pellets (48 g, 0.85 mol, 1.8 equivalents). The reaction was then heated to reflux for 30 minutes. The mixture was cooled to room temperature and concentrated in vacuo to afford a milky suspension. This mixture was diluted with water (100 mL), cooled to 0° C., and acidified with concentrated hydrochloric acid (15 mL) to pH 6. Additional water (100 mL) was added, and the mixture extracted with ethyl acetate (3×400 mL). The combined organics were washed with water (1×600 mL), saturated aqueous chloride solution (1×600 mL), dried over anhydrous magnesium sulfate, and filtered. The filtrate was concentrated in vacuo to afford a pale yellow oil which on drying in vacuo afforded 59 g (94% yield) of (8) as a crystalline solid. The $^1$H NMR of the product was consistent with the material previously prepared.

Preparation of (2S)-(+)-N-methoxy-N-methyl-2,3-dimethyl-2-hydroxybutyramide (9)

To a magnetically stirred solution of (8) (59 g, 0.44 mol) in methylene chloride (880 mL) in a 3-L, two-neck, round-bottom flask at 0° C. under a nitrogen atmosphere was added 1,1-carbonyldiimidazole (87 g, 0.54 mol, 1.2 equivalents) in portions. The yellow solution was gradually warmed to room temperature and stirred under a nitrogen atmosphere overnight. To the reaction was added imidazole (60 g, 0.88 mol, 2 equivalents), 4-dimethylaminopyridine (1.6 g, 0.01 mol, 0.03 equivalents), and N,O-dimethylhydroxylamine hydrochloride (53 g, 0.54 mol, 1.2 equivalents). The solution was stirred overnight and then the resulting mixture was washed with 2N aqueous hydrochloric acid (2×600 mL), water (1×800 mL), and saturated aqueous sodium chloride solution (1×800 mL), dried over anhydrous magnesium sulfate, and filtered. The solvent was removed in vacuo to provide 73 g (94% yield) of (9) as a yellow oil. The $^1$H NMR spectrum of the product was consistent with the material previously prepared.

Preparation of (2S)-(+)-N-methoxy-N-methyl-2,3-dimethyl-2-triethylsilyloxybutyramide (10)

To a magnetically stirred solution of (9) (25 g, 0.14 mol) in N,N-dimethylformamide (400 mL) in a 1-L, round-bottom flask under a nitrogen atmosphere was added imidazole (20 g, 0.29 mol, 2 equivalents), followed by triethylsilyl chloride (24.1 g, 0.16 mol, 1.1 equivalents). The resulting solution was allowed to stir under a nitrogen atmosphere overnight. The reaction was then diluted with ether (800 mL), and washed with water (600 mL). The aqueous layer was extracted with ether (2×400 mL), and the combined organics washed with saturated aqueous sodium chloride solution (2×600 mL), dried over anhydrous magnesium sulfate, and filtered. The filtrate was evaporated in vacuo to provide a yellow oil (45 g). Column chromatography (9:1 hexanes:ethyl acetate) afforded 29 g (72% yield) of (10) as a pale yellow oil. The $^1$H NMR spectrum of the product was consistent with the structure.

Preparation of (2S)-(+)-2,3-dimethyl-2-triethylsilyloxybutyraldehyde (2)

Figure 4:
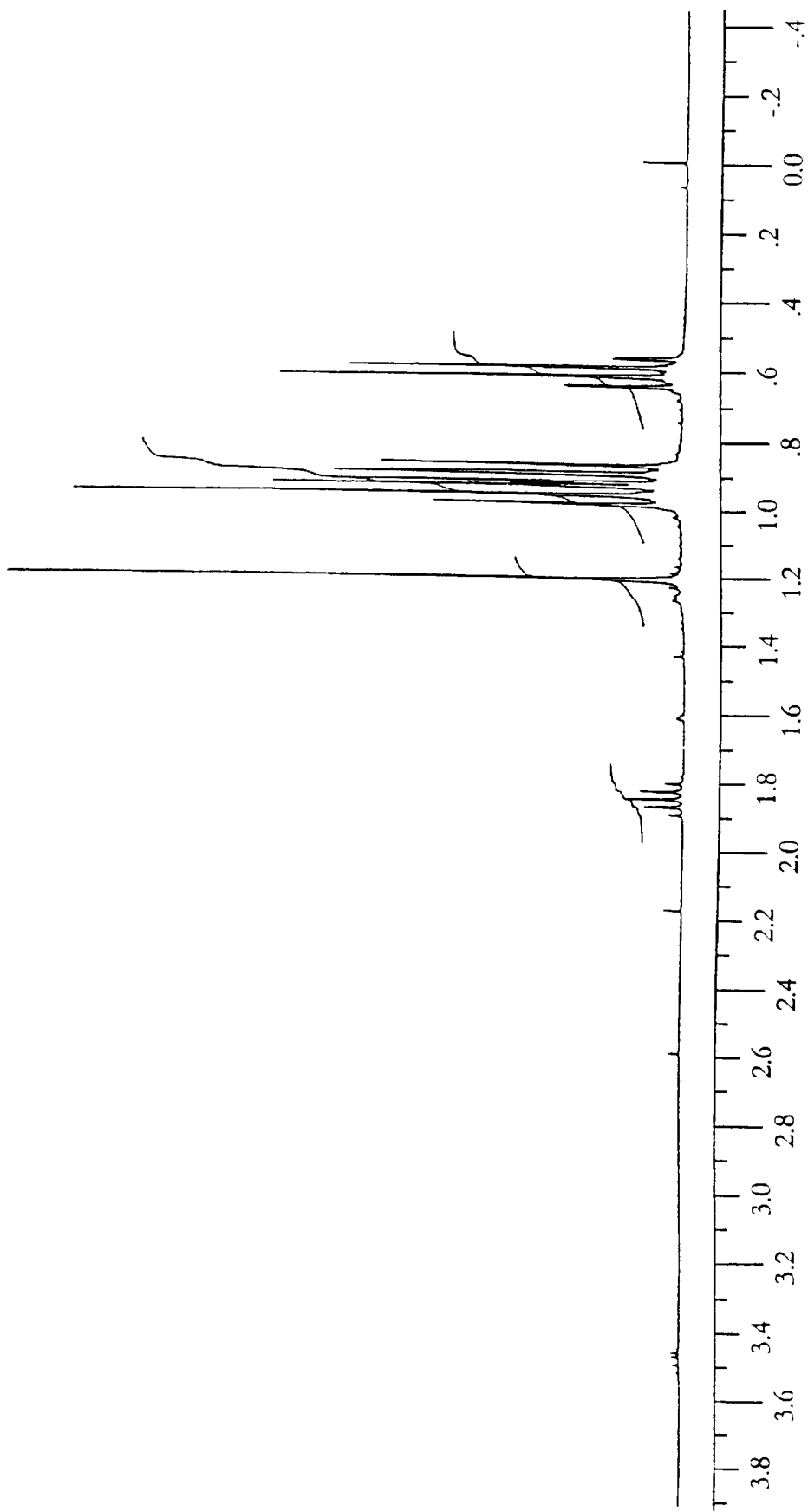
FIG. 4 is an NMR spectrum of the (S)-(+)-2,3-dimethyl-2-triethylsilyloxybutyraldehyde of the reaction scheme of FIG. 1.

In a 5-L, three-neck, round-bottom flask equipped with a mechanical stirrer, thermocouple, pressure equalizing addition funnel, and nitrogen bubbler was added a solution of (10) (66 g, 0.23 mol) in dry THF (2 L). The reaction was cooled to −60° C. and maintained under an atmosphere of dry nitrogen. Diisobutylaluminum hydride (1.0 M solution in toluene, 460 mL, 0.46 mol, 2.0 equivalents) was transferred to the addition funnel and slowly added to the reaction solution over 20 minutes. The resulting solution was stirred for three hours until TLC analysis (silica gel plates eluted with 4:1 hexanes:ethyl acetate) indicated no more starting material was present. At this point, potassium tartrate (108 g) was added, and the resulting white slurry was stirred overnight at room temperature. The reaction mixture was evaporated in vacuo to 25% of the original volume. The mixture was then diluted with ethyl acetate (1 L) and Celite™ was added. The resulting thick slurry was filtered through a plug of silica gel. The filtrate was evaporated in vacuo to afford a yellow oil (48 g). Silica gel column chromatography (5% ethyl acetate in hexanes) provided 40 g (74% yield) of (2) as a colorless oil. The $^1$H NMR spectrum was consistent with the desired product. (See, FIG. 4.)

EXAMPLE 2

Synthesis of the vitamin D phosphine oxide (3)
Preparation of $SO_2$-adduct of (3S)-tert-butyldimethylsiloxy-9,10-secoergosta-5,7(E), 10(19), 22(E)-tetraene (11)

Sulfur dioxide (approximately 300 mL) was condensed at −78° C. into a 2-L, three-neck, round-bottom flask equipped with a dry ice condenser, thermocouple, pressure-equalizing addition funnel, and a mechanical stirrer. To this was added a solution of ergocalciferol (vitamin $D_2$) (198 g, 0.50 mol) in methylene chloride (500 mL) producing a bright yellow mixture, which progressively turned to a red color. The flask was then attached to two sequential gas scrubber systems (using 15 M aqueous sodium hydroxide solution), and the reaction was allowed to gradually warm to −10° C. over a three-hour period. At this point, the solvent was removed in vacuo to afford a crude foam. This foam was dissolved in fresh methylene chloride (700 mL) and cooled to 5° C. To this solution was added imidazole (44 g, 0.65 mol, 1.3 equivalents) producing an orange solution which was stirred for 15 minutes. At this time, tert-butyldimethylsilyl chloride (98 g, 0.65 mol, 1.3 equivalents) was added, producing a milky, yellow suspension. The suspension was gradually warmed to room temperature where it was stirred for 17 hours. The reaction was filtered through a Celite™ pad and the residue was washed with methylene chloride (2×400 mL). The combined filtrates and washings were washed with saturated aqueous sodium chloride solution (2×500 mL), dried over anhydrous magnesium sulfate, and filtered. The filtrate was evaporated in vacuo to afford 288 g of (11) as a pale yellow foam. This material was used in the next step without purification.

Preparation of $SO_2$-adduct of (3S)-tert-butyldimethylsilyloxy-(20S)-hydroxymethyl-9,10-secopregna-5(Z),7(E),10(19)-triene (12)

To a solution of (11) (288 g, 0.50 mol) in methylene chloride (2.9 L) and methanol (1.1 L) in a 12-L, three-neck, round-bottom flask equipped with a gas bubbler, mechanical stirrer, thermocouple, and a reflux condenser was added sodium acetate (41 g, 0.5 mol, 1 equivalent), and acetic acid (29 mL). This mixture was cooled to −25° C. and ozone (generated from air, using a Griffin ozone generator) was bubbled through the solution for 4.5 hours or until TLC analysis (silica gel plates eluted with 4:1 hexanes:ethyl acetate) indicated no more change. The resulting mixture was purged with nitrogen for 15 minutes and sodium borohydride (69 g, 1.81 mol, 3.6 equivalents) was added in portions over one hour. The resulting mixture was allowed to stir for 1.5 hours at room temperature. At this point, 0.5 N aqueous hydrochloric acid solution (2.9 L) was added slowly, and the mixture extracted with hexanes (3.5 L). The combined organics were washed with saturated aqueous sodium chloride solution (2×4 L), dried over anhydrous magnesium sulfate, and filtered. The filtrate was evaporated in vacuo to afford 274 g of (12) as a yellow foam which was used as is. This material was used in the next step without purification.

Preparation of $SO_2$-adduct of (3S)-tert-butyldimethysilyloxy-(20S)-iodomethyl-9,10-secopregna-5(Z),7(E),10(19)-triene (13)

A 12-L, three-neck, round-bottom flask equipped with a mechanical stirrer, thermocouple, nitrogen bubbler, and an additional funnel, was charged with imidazole (204 g, 2.99 mol, 6.0 equivalents), triphenylphosphine (300 g, 1.14 mol, 2.3 equivalents), and methylene chloride (2.5 L). The resulting solution was cooled to −2° C. and to this was added iodine (290 g, 1.14 mol, 2.3 equivalents). The resulting mixture was allowed to stir for 15 minutes, and then a solution of (12) (274 g, 0.50 mol) in methylene chloride (1.3 L) was added slowly, over 35 minutes. The resulting orange mixture was allowed to warm to room temperature where it was stirred for three hours. The reaction mixture was filtered, and the filtrate was washed successively with 2% aqueous sodium sulfite solution (1×2 L), 0.1 N aqueous hydrochloric acid solution (1×1.5 L), and saturated aqueous sodium chloride solution (1×1.5 L). The organics were then dried over anhydrous magnesium sulfate and filtered. The solvent was removed in vacuo to afford a yellow residue which was dissolved in ether (4 L) producing a white precipitate (triphenylphosphine oxide). The solution was filtered and the filtrate was evaporated in vacuo to afford 320 g of (13) as a yellow oil contaminated with triphenylphosphine oxide. This material was used in the next step without purification.

Preparation of (3S)-tert-butyldimethylsilyloxy-(20S)-iodomethyl-9,10-secopregna-5(Z),7(E),10(19)-triene (14)

A 12-L, three-neck flask equipped with a reflux condenser, mechanical stirrer and a stopper was charged with (13) (308 g), sodium bicarbonate (309 g, 3.7 mol, 7.3 equivalents), and a 95% ethanol solution (5 L). The resulting suspension was heated under reflux for two hours or until TLC analysis (silica gel plates eluted with 2% ethyl acetate in hexanes) indicated no more starting material. The reaction was cooled to room temperature, and the solvent was removed in vacuo. The crude residue was dissolved in ether (3 L) and washed with water (5 L). The aqueous layer was back extracted with ether (3 L). The combined ether extracts were dried over anhydrous magnesium sulfate and filtered through a Celite™ pad. The filtrate was evaporated in vacuo to afford a yellow foam (277 g). Silica gel column chromatography (eluted with 1% ethyl acetate in hexanes) provided (14) as a white solid (93.7 g). The impure fractions were subjected to repeated silica gel column chromatographic purification to afford an additional crop of iodide (14) (46 g). Overall yield for the three steps was 51%. The $^1$H NMR spectrum of the product was consistent with the structure.

Preparation of (3S)-tert-butyldimethylsilyloxy-(20S)-(diphenylphosphonium)-9,10-secopregna-5(Z),7(E),10(19)-triene (3)

Figure 5:
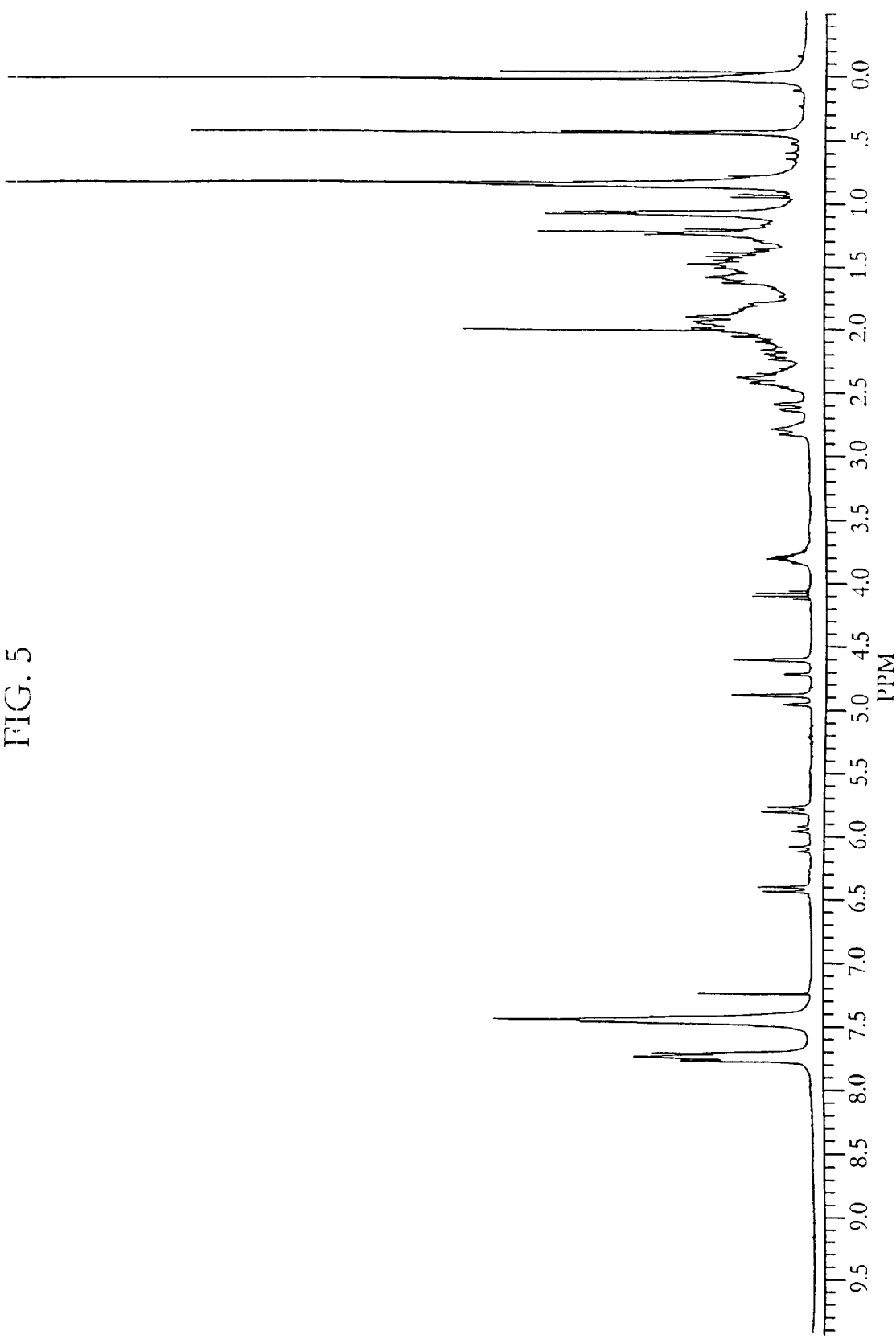
FIG. 5 is an NMR spectrum of the vitamin D phosphine oxide formed from the reaction scheme of FIG. 2.

In a 5-L, three-neck, round-bottom flask equipped with a mechanical stirrer, thermocouple, and nitrogen bubbler, and two pressure equalizing addition funnels was added diphenylphosphine (41 g, 0.22 mol). Dry THF (570 mL) was added and the stirred solution was cooled to −78° C. To one of the addition funnels was added, via a cannula, n-butyllithium (2.5 M solution in hexanes, 90 mL, 0.23 mol, 1.3 equivalents). This was slowly added to the reaction solution producing a reddish-orange mixture which was stirred at −78° C. for 45 minutes. A solution of (14) (94 g, 0.17 mol) in dry THF (570 mL) was transferred to the second addition funnel, and this solution was slowly added to the reaction mixture over 20 minutes. The resulting pale yellow solution was stirred for 45 minutes at −78° C. and then gradually warmed to room temperature where it was stirred for three hours. The reaction mixture was diluted with ether (4 L) and washed with saturated aqueous ammonium chloride solution (1×2 L). The organic layer was first washed with 10% hydrogen peroxide (3×1L). The organic layer was then washed with saturated aqueous sodium chloride solution (2×1.5 L), dried over anhydrous magnesium sulfate, and filtered. The yellow filtrate was evaporated in vacuo to afford a crude yellow residue (140 g). Column chromatography (5% ethyl acetate in hexanes/30% ethyl acetate in hexanes) provided 88 g (83% yield) of (3) as a glassy solid. The $^1$H NMR spectrum of the product (3) was consistent with the structure. (See, FIG. 5.)

EXAMPLE 3

Synthesis of 24(S)-Hydroxyvitamin $D_2$ (1)

Preparation of the silyl-protected trans-24(S)-hydroxyvitamin $D_2$ (16)

In a 3-L, three-neck, round-bottom flask equipped with a mechanical stirrer, thermocouple, addition funnel, and a nitrogen bubbler was added a solution of (3) (47.1 g, 74.9 mmol) in dry THF (700 mL). The solution was cooled to −75° C. and n-butyllithium (2.5 M solution in hexanes, 60 mL, 150.0 mmol, 2.0 equivalents) was added, producing a red solution which was stirred for 45 minutes. At this point, a solution of (2) (22.3 g, 96.8 mmol, 1.3 equivalent) in THF was slowly added. This solution was stirred vigorously at −75° C. for one hour, producing a yellow solution. The solution was allowed to warm to 0° C. over 1.5 hours. The reaction solution was then diluted with ethyl acetate, and washed with saturated aqueous ammonium chloride solution (1×800 mL), water (1×800 mL), and saturated aqueous sodium chloride solution (1×800 mL). The organic layer was dried over anhydrous magnesium sulfate, filtered, and the solvent evaporated in vacuo to afford a yellow oil (72 g). This was dissolved in dry THF (1.3 L) and transferred to a 3-L, three-neck, round-bottom flask equipped with a mechanical stirrer, thermocouple, a nitrogen bubbler, and a rubber septum. The reaction was cooled to −12° C. and potassium tert-butoxide (70 g, 62.4 mmol, 8.4 equivalents) was added, producing an orange mixture. The reaction was allowed to stir at this temperature for 2.5 hours at which point it was diluted with ethyl acetate (1.4 L), and washed successively with 0.01 N aqueous hydrochloric acid solution (2×1 L), water (1×1 L), and saturated aqueous sodium chloride solution (1×1 L). The organics were dried over anhydrous magnesium sulfate, filtered, and the solvent evaporated in vacuo producing 58 g of (16) as a yellow oil. This oil was used directly in the next step without purification.

Preparation of trans-(24S)-Hydroxyvitamin $D_2$ (17)

To a solution of (16) (48 g, 74.9 mmol) in dry THF (1 L) at 0° C in a 3-L, three-neck, round-bottom flask equipped with a mechanical stirrer, a rubber septum, and an addition funnel was slowly added tetra-butylammonium fluoride (1.0 M solution in THF, 500 mL, 500 mmol, 7.0 equivalents). The resulting dark-colored solution was allowed to stir at 0° C. for one hour and slowly warmed to room temperature where it was stirred for 48 hours. At this point, the reaction mixture was diluted with water (1.5 L) and extracted with ethyl acetate (2×1 L). The combined extracts were washed with 0.01 N aqueous hydrochloric acid solution (1×1 L) and saturated aqueous sodium chloride solution (2×1.5 L), dried over anhydrous magnesium sulfate, and filtered. The filtrate was concentrated in vacuo to afford an orange oil (58.5 g). Column chromatography (4:1 hexanes:ethyl acetate) provided 9.5 g of (17) as a white foam in overall yield of 31% from (3). The $^1$H NMR spectrum was consistent with the structure.

Preparation of (24S)-hydroxyvitamin $D_2$ (1)

Figure 6:
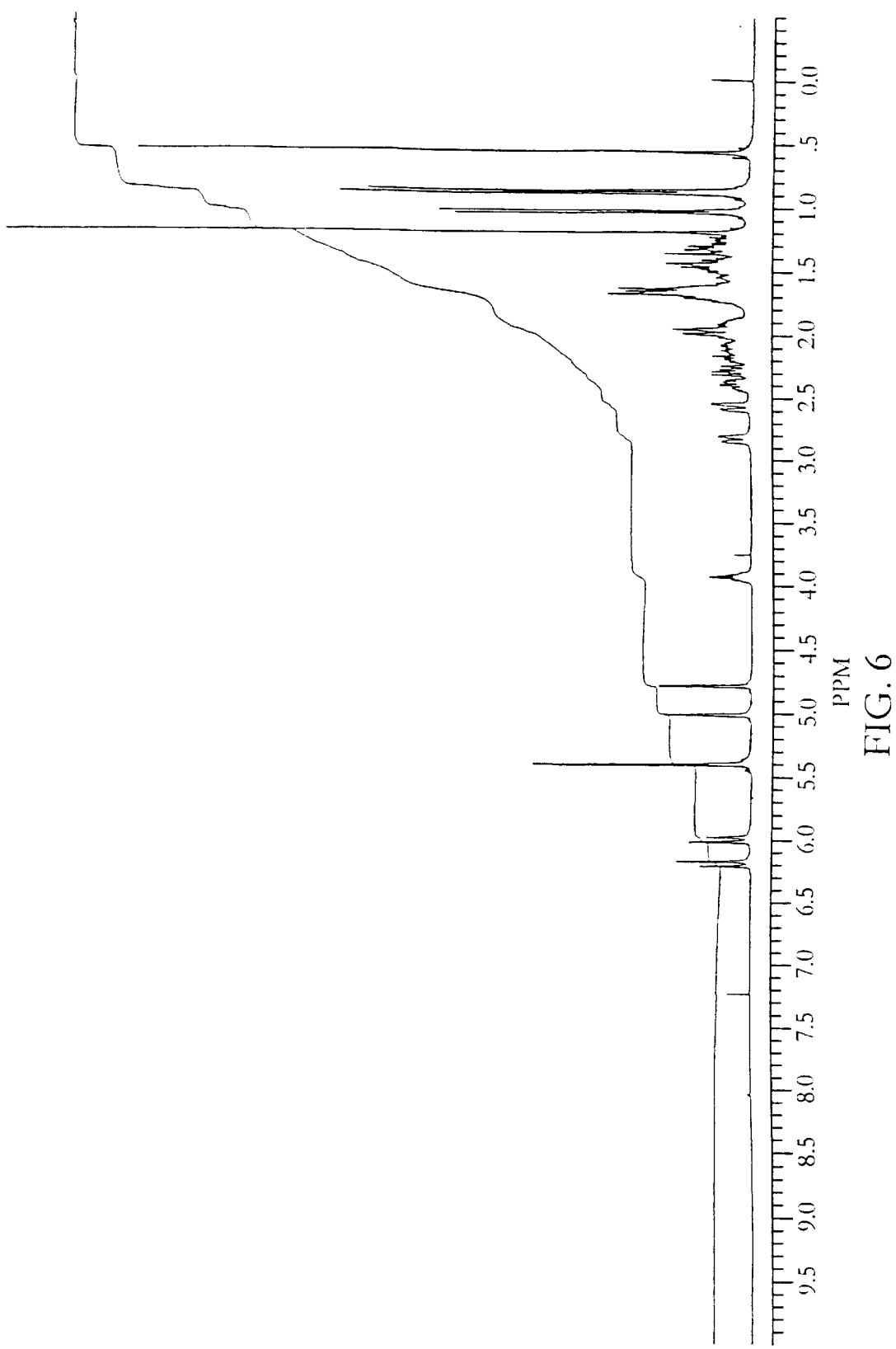
FIG. 6 is a proton NMR spectrum of 24(S)-hydroxyvitamin D$_2$ prepared by the method of the present invention.
Figure 7:
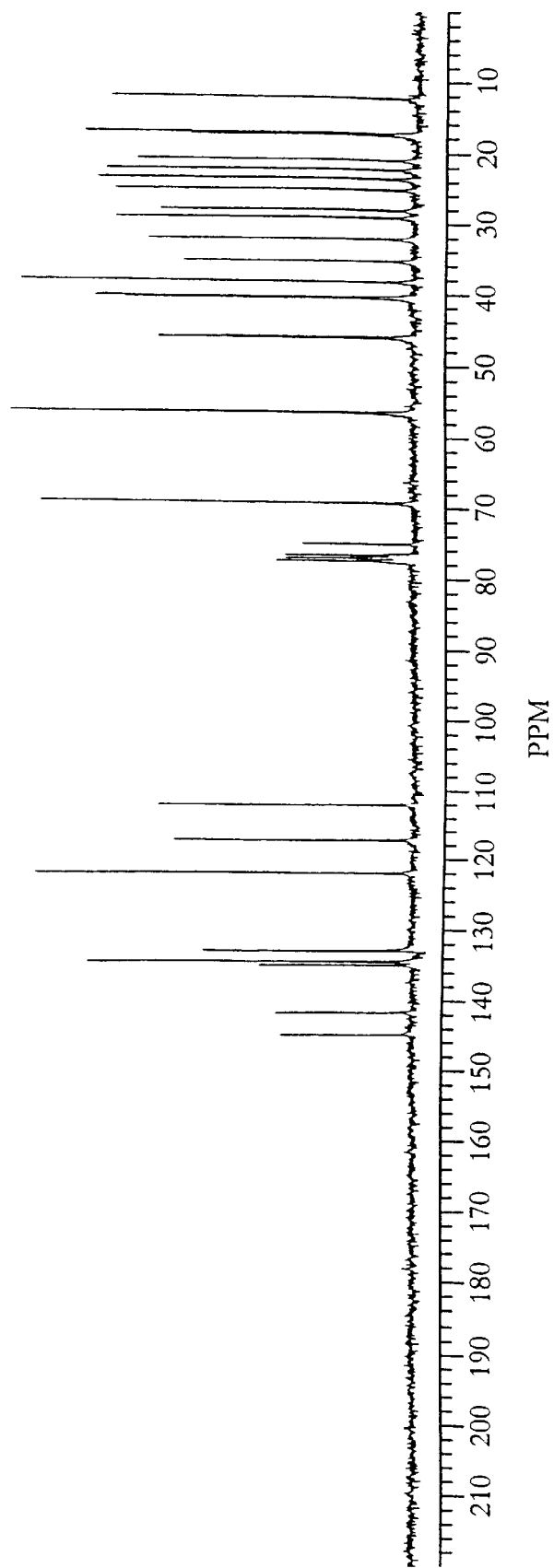
FIG. 7 is an NMR spectrum of 24(S)-hydroxyvitamin D$_2$ prepared by the method of the present invention.
Figure 8:
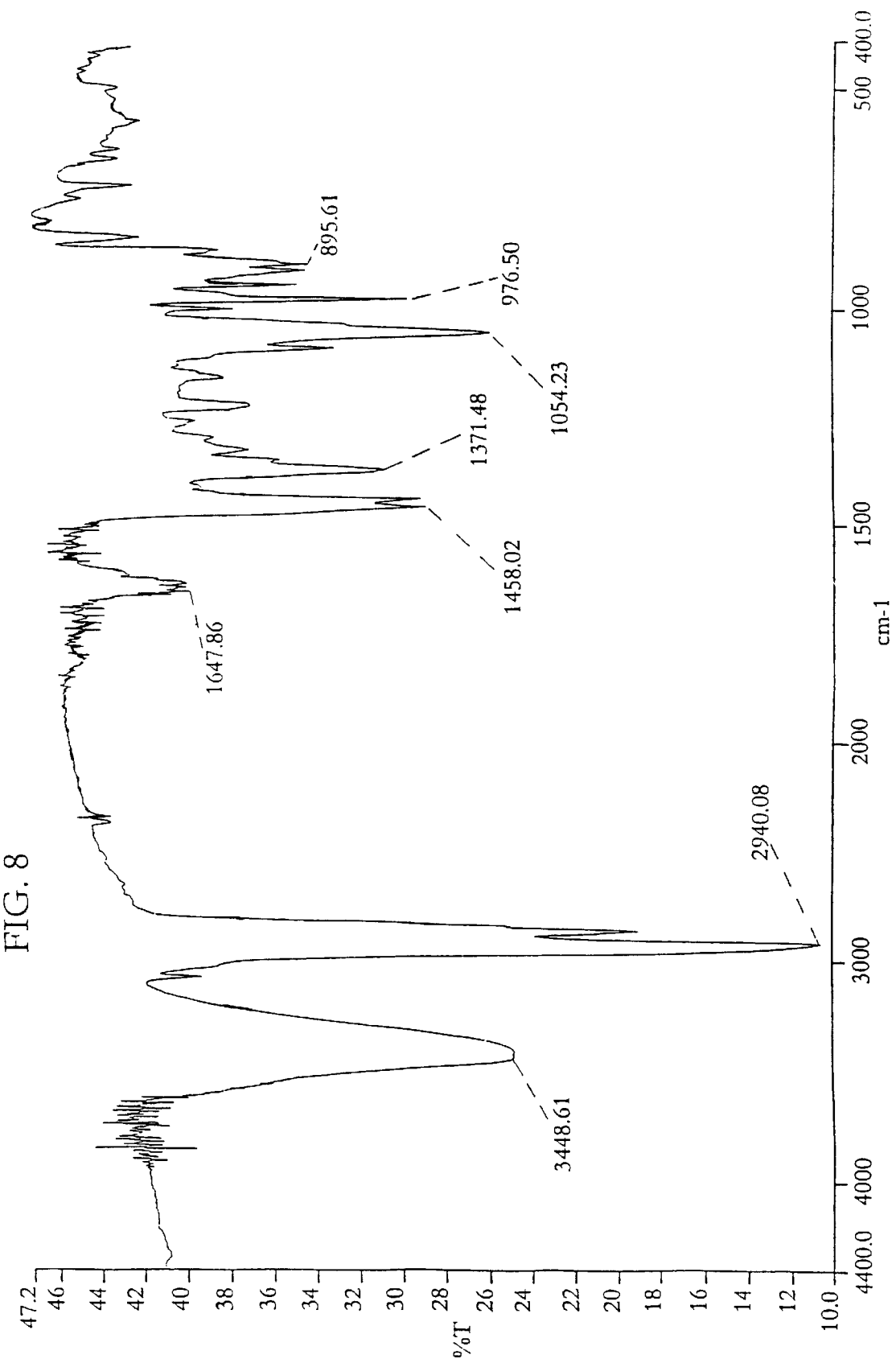
FIG. 8 is an IR spectrum of 24(S)-hydroxyvitamin D$_2$ prepared by the method of the present invention.

A 4-L photoreactor was charged with a solution of (17) (9.5 g, 23 mmol) and 9-acetylanthracene (1.2 g, 6 mmol) in methanol (4 L). The resulting solution was cooled to 7° C. and purged with nitrogen for 1.5 hours. It was then irradiated using a 400 W Hanovia Lamp through a uranium filter for one hour. An aliquot (20 mL) was taken and evaporated in vacuo. The $^1$H NMR spectrum of the crude residue showed the reaction to be complete. The solvent was then removed in vacuo to afford a yellow oil (12.1 g). Another photoisomerization was carried out using the same protocol on (17) (7.2 g, 17.4 mmol) and 9-acetylanthracene (1.5 g, 7 mmol) in methanol (4 L) to afford a yellow oil (8.1 g). Column chromatography on both lots (4:1 hexanes:ethyl acetate) afforded (1) (13.3 g, 80%) as a white solid. Recrystallization from methyl formate afforded 9.9 g of (1) as white crystals. A second crop of crystals, obtained on concentration of the mother liquor, afforded an additional 1.1 g of (1) (total yield 83%; see, FIGS. 6, 7 and 8) (mp 129–130° C. (methyl formate); $[\alpha]_D^{24.5° C.}=+123.7°$(c=1.0, EtOH); TLC analysis $R_f$=0.10 (4:1 hexanes:ethyl acetate; silica, Whatman Number 4500-101). Elemental analysis calculated for $C_{28}H_{44}O_2$: C, 81.50; H, 10.75. Found: C, 81.56; H, 10.49.

In summary, the present invention provides a method of preparing 24(S)-hydroxyvitamin $D_2$ via a coupling reaction in which the ultimate product has the desired stereospecificity rather than resulting in a diastereomeric mixture that requires separation.

While the present invention has now been described and exemplified with some specificity, those skilled in the art will appreciate the various modifications, including variations, additions and omissions, that may be made in what has been described. Accordingly, it is intended that these modifications also be encompassed by the present invention and that the scope of the present invention be limited solely by the broadest interpretation that lawfully can be accorded the appended claims.

What is claimed is:

1. A method of preparing 24(S)-hydroxyvitamin $D_2$ comprising the steps of (a) coupling (S)-(+)-2,3-dimethyl-2-triethylsilyloxybutyraldehyde and a C-22 vitamin D phosphine oxide derivative to form a 3,24-diprotected trans-vitamin $D_2$;

(b) deprotecting the trans-vitamin $D_2$; and then (c) isomerizing the trans-vitamin $D_2$ to the 24(S)-hydroxy-vitamin $D_2$.

2. The method of claim 1, wherein the coupling step (a) is accomplished with n-butyllithium followed by potassium t-butoxide.

3. The method of claim 1, wherein the deprotecting step (b) is accomplished with tetrabutylammonium fluoride.

4. The method of claim 1, wherein the isomerizing step (c) is accomplished with irradiation at 366 nm.

* * * * *

UNITED STATES PATENT AND TRADEMARK OFFICE
CERTIFICATE OF CORRECTION

PATENT NO. : 6,359,012 B1
APPLICATION NO. : 09/470581
DATED : March 19, 2002
INVENTOR(S) : Harold Meckler et al.

It is certified that error appears in the above-identified patent and that said Letters Patent is hereby corrected as shown below:

Title Page     Item (56)   Col. 1   Page 2
Please list the following references under "References Cited."

Koch, P., et al., "A Stereoselective Synthesis and a Convenient Synthesis of Optically Pure (24 R)- and (24 S)- 24-hydroxycholesterols", Soc. Chim. Fr., Vol. 2, no. 7/8, pp. 189-194 (1983).

McPherson et al., "Structure Elucidation Via Stereoselective Synthesis of the Acetate Center of 1-Azabicyclo [2.2.2]oct-3-yl · Hydroxy-·-(1-iodo-1-propen-3-yl)-·-phenylacetate (IQNP). A High Affinity Muscarinic Imaging Agent for SPECT", J. Org. Chem., Vol. 61, no. 23, pp. 8335-8337 (1996).

Geffken, D., et al., "3-Substituted 1-Alkoxyindolin-2-ones from N-Alkoxy-2-phenylglycolamides and Dicyclohexylcarbodiimide", Naturforsch. B. Anorg. Chem. Org. Chem., Vol. 40, no. 3, pp. 398-401 (1985).

Baxter, J., et al., "An Approach to the Synthesis of the C(17)-C(27) Fragment of Bryostatins", Tetrahedron, Vol. 54, no. 47, pp. 14359-14376 (1998).

Column 3, Line 26
"D2 24(S)-hydroxyvitamin" should read --D2. 24(S)-hydroxyvitamin--.

Column 4, Line 63
"L-15 (+)-valine" should read --L-(+)-valine--.

Signed and Sealed this

Twenty-second Day of August, 2006

JON W. DUDAS
*Director of the United States Patent and Trademark Office*